United States Patent [19]

Schoenberg

[11] Patent Number: 4,996,268

[45] Date of Patent: Feb. 26, 1991

[54] CARBINOL-CONTAINING POLYIMIDE OLIGOMERS TERMINATED WITH EPOXIDE-REACTIVE GROUPS

[75] Inventor: Jules E. Schoenberg, Scotch Plains, N.J.

[73] Assignee: National Starch and Chemical Investment Holding Corporation, Wilmington, Del.

[21] Appl. No.: 312,106

[22] Filed: Feb. 17, 1989

Related U.S. Application Data

[62] Division of Ser. No. 880,884, Jul. 1, 1986, Pat. No. 4,820,779.

[51] Int. Cl.$^5$ ............... C08G 73/10; C08G 73/14; C08G 73/16
[52] U.S. Cl. ............................ 525/434; 525/533; 528/222; 528/229; 528/351
[58] Field of Search ............... 525/423, 533, 434, 435; 528/222, 224, 229, 351

[56] References Cited

U.S. PATENT DOCUMENTS

| | | | |
|---|---|---|---|
| 4,041,004 | 8/1977 | Barie et al. | 260/32.8 |
| 4,277,583 | 7/1981 | Waitkus et al. | 525/423 |
| 4,410,664 | 10/1983 | Lee | 525/180 |
| 4,487,894 | 12/1984 | Lee | 525/423 |
| 4,489,185 | 12/1984 | Schoenberg | 528/229 |
| 4,519,941 | 5/1985 | Anderson | 524/439 |

FOREIGN PATENT DOCUMENTS

| | | |
|---|---|---|
| 0077718 | 4/1983 | European Pat. Off. |
| 49-38119 | 10/1974 | Japan |
| 51-131526 | 11/1976 | Japan |

*Primary Examiner*—John C. Bleutge
*Assistant Examiner*—Robert E. L. Sellers, II
*Attorney, Agent, or Firm*—Edwin M. Szala

[57] ABSTRACT

A carbinol-containing polyimide oligomer terminated with epoxide-reactive end groups has the structure

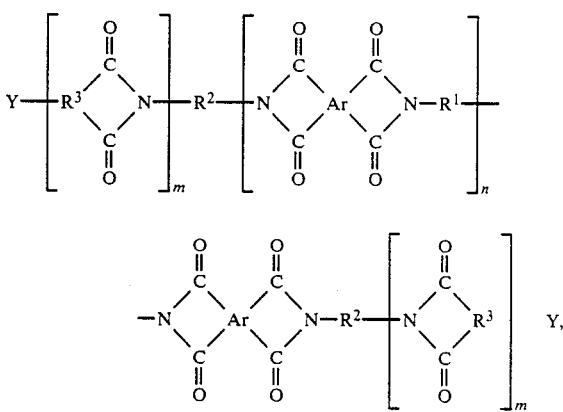

wherein Ar is

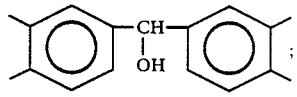

$R^1$ and $R^2$ are independently divalent organic radicals; $R^3$ is a trivalent organic radical; Y is an epoxide-reactive group (e.g.); m is 0 or 1 and n is 0–10. Suitable epoxide-reactive groups include a phenol, thiol, amine, or carboxyl group. Polyimide-polyepoxide adducts are prepared by reacting the polyimides with a polyepoxide, preferably a diepoxide used in excess. The polyimide oligomers are useful as coatings or adhesives. The adducts are useful as adhesives, for composites, and particularly for impregnating the fiberglass sheets which are used to form circuit boards.

7 Claims, No Drawings

CARBINOL-CONTAINING POLYIMIDE OLIGOMERS TERMINATED WITH EPOXIDE-REACTIVE GROUPS

This application is a division of application Ser. No. 880,884, filed Jul. 1, 1986, now U.S. Pat. No. 4,820,779.

BACKGROUND OF THE INVENTION

This invention relates to carbinol-containing polyimide oligomers terminated with selected epoxide-reactive groups and to the reaction products thereof with polyepoxides.

Polyepoxides are thermosetting resins which can be cured at reasonably low temperatures with little or no by-product formation. They are viscous liquids or brittle solids which are noted for low shrinkage, lasting adhesion, high dieletric strength and chemical resistance; however, they lose strength at high temperatures. They are useful as coatings, adhesives, or molding compounds.

Polyimides are synthetic organic resins characterized by repeating imide linkages in the polymer chain. They are noted for their outstanding chemical and physical properties, particularly their high temperature oxidative stability and strength. They are likewise useful as coatings, adhesives, and composites. Most polyimides, especially the preferred aromatic polyimides, are extremely difficult to process due to their extremely high softening points as well to their insolubility in organic solvents.

Various methods have been used to insure processibility, such as the use of the polyamic acid intermediates or low molecular weight polyimides terminated with unsaturated polymerizable groups. The solubility has been improved by the use of selected carbinol-containing polyimides, as disclosed in European patent application No. 82401866.7 filed Oct. 11, 1982 and published under No. 0 077 718 on Apr. 27, 1980 and in U.S. Pat. No. 4,489,185 issued to J. E. Schoenberg on Dec. 18, 1984.

Polyimides have been combined with polyepoxides and crosslinked with or without typical epoxy catalysts such as amines or anhydrides. The carbinol-containing polyimides described in the above European patent application have also been combined with a polyepoxide (see Example 18) and cured to an insoluble, infusible state by evaporating off the solvent and heating for 30 minutes at 190° C. The problem with these prior art combinations is that the two part systems are frequently mutually incompatible and the curing reaction which takes place between the polyimide and the polyepoxide is poorly controlled.

There is a need for a polyimide-polyepoxide adduct with improved processibility (e.g., good solubility in organic solvents) and an intermediate Tg.

SUMMARY OF THE INVENTION

The present invention provides a carbinol-containing polyimide oligomer terminated with epoxide-reactive end groups, which has the structure

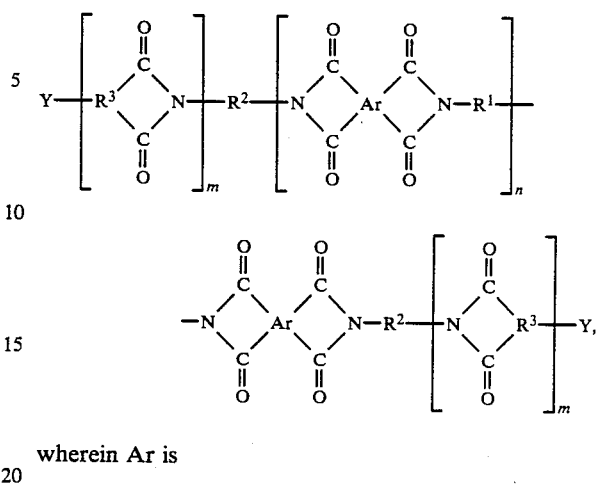

wherein Ar is

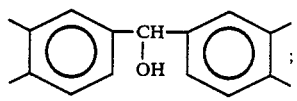

$R^1$ and $R^2$ are independently divalent organic radicals; $R^3$ is a trivalent organic radical; Y is an epoxide-reactive group; m is 0 or 1; and n is 0–10. Suitable epoxide-reactive groups include phenols, thiols, amines, and carboxyls, with the phenols and carboxyls being preferred.

When n and m are 0, the polyimide is prepared by reacting a primary amine containing the epoxide-reactive group with a carbinol-containing tetracarboxylic acid compound. When n is 1 or greater and m is 0, the polyimide is prepared by reacting a primary polyamine, preferably a diamine, with an excess of a carbinol-containing tetracarboxylic acid compound and with a primary amine containing an epoxide-reactive group. When m is 1 and n is 0 or greater, the polyimide is prepared by reacting the carbinol-containing tetracarboxylic acid compound with an excess of a primary polyamine, preferably a diamine, and with a dicarboxylic acid compound containing the epoxide-reactive group. Suitable carbinol-containing tetracarboxylic acid compounds are described in U.S. Pat. No. 4,489,185, the disclosure of which is incorporated herein by reference. The use of polyamines may yield a product that may crosslink with the epoxide prior to heat curing.

The present invention also provides polyimide-polyepoxide adducts which are prepared by reacting the above carbinol-containing polyimides terminated with epoxide-reactive groups with polyepoxide. When the polyepoxide is a diepoxide used in excess, the adduct has the structure

with p being determined by the ratio of diepoxide to polyimide.

The carbinol-containing polyimide oligomers terminated with epoxidereactive end groups are useful as coating or adhesives. The adducts prepared by the reaction of these polyimide oligomers with polyepoxides, preferably diepoxides, are useful as adhesives, for composites, and particularly for impregnating the fiberglass sheets which are used to form circuit boards.

DESCRIPTION OF THE PREFERRED EMBODIMENTS

The polyimides useful herein are soluble polyimides (typically n is 0 to 10) containing carbinol moieties and preferably flexibilizing moieties. They are terminated with end groups reactive with epoxide groups. Typically, they are prepared by reacting a suitable carbinol-containing tetracarboxylic acid compound (e.g., the bis(methyl half-ester) of 3,3',4,4'-benzhydroltetracarboxylic acid) with a polyfunctional aliphatic, cycloaliphatic, aromatic or heterocyclic primary polyamine, preferably an asymmetric diamine or a diamine containing flexibilizing moieties, and a primary amine containing the epoxide-reactive end group or a dicarboxylic acid compound containing the epoxide reactive end group. The reaction is carried out in an inert organic solvent which is a solvent for the polyimide. The temperature used should be sufficient to effect polymerization and imidization (i.e., ring closure to the imide).

Suitable diaryl carbinol-containing tetracarboxylic acid compounds include tetraacids, dianhydrides, and preferably diester-diacids such as 3,3',4,4'-benzhydroltetracarboxylic acid, the dianhydride thereof, or the diester-diacid thereof, e.g., bis(methyl half ester) whose preparation is described in Example I. Such tetracarboxylic acid compounds are disclosed in U.S. Pat. No. 4,489,185 and European patent application No. 82401866.7 (cited previously).

Suitable polyamines include the aliphatic, cycloaliphatic, heterocyclic, and aromatic amines well-known in the art and listed in U.S. Pat. No. 3,528,950 issued Sept. 15,1970 to H. R. Lubowitz. Among the preferred aromatic diamines are 4,4'-oxydianiline, 3,3'-sulfonyldianiline, 4,4'-bis(3-aminobenzoyl)diphenyl ether, 1,3-bis(3-aminophenoxy) benzene, 2,4-toluenediamine, and diethyltoluene-diamine. Aliphatic diamines suitable for use herein include bis(3-aminopropyl)tetramethyl disiloxane and 1,6-hexanediamine.

Suitable terminating compounds are primary amines containing an epoxide-reactive group (e.g., p- or m-aminophenol or p- or m-aminobenzoic acid) or dicarboxylic acid compounds containing an epoxide-reactive group (e.g., trimellitic anhydride).

The reactions are carried out in a suitable inert organic solvent under anhydrous conditions, preferably using pure monomers and dry solvent. The solvent used should dissolve at least one of the reactants, preferably all of the reactants, as well as the final polyimide and its adduct with the polyepoxide. Polar solvents are preferred. Suitable solvents include, for example, glycol ethers, amides, dimethyl sulfoxide, dimethylsulfone, tetramethylurea, dioxane, 1-methyl-2-pyrrolidinone, N-acetylpyrrolidinone, hexamethylphosphoramide, tetramethylenesulfone, and the like. These solvents can be used alone or in combination with other solvents such as benzene, benzonitrile, dioxane, xylene, toluene, and cyclohexane. The preferred solvents are 1-methyl-2-pyrrolidinone and 2-methoxyethyl ether. Reaction conditions used for the preparation of the polyimides herein will depend upon the tetracarboxylic acid compound, terminating compound used, and polyamine, if any, used as well as the solvent selected and the concentration and molecular weight of the final polyimide.

When m equals zero, the ratio of tetracarboxylic acid compound to diamine to primary amine containing the epoxide-reactive group is n+1:n:2 and n is between 0 and 10. Thus, it is 1:0:2 when no diamine is used in the reaction (where n is 0) and between 2:1:2 and 11:10:2 when all three compounds are used in the reaction (where n is 1-10), preferably 2:1:2 to 6:5:2 (where n is 1-5). When the terminal group contains an amine as the epoxide-reactive group and it is derived from the diamine used for the formation of the other imide groups, the ratio of tetracarboxylic acid compound to polyamine is n+1:n+2 and $R^1$ is the same as $R^2$ unless a mixture of diamines is used. When m is 1, the ratio of tetracarboxylic acid compound to diamine to dicarboxylic compound containing the epoxide-reactive group is n+1:n+2:2 and n is between 0-10. It is between 1:2:2 and 11:12:2, preferably 2:3:2 to 6:7:2. The molecular weight is controlled by the stoichiometry.

It is possible to recover the polyimide resin in dry form (by precipitation with a non-solvent such as water). If this is done, it is then possible to prepare the adduct in a different solvent.

In one method, the 3,3',4,4'-benzophenonetetracarboxylic dianhydride is reacted with an anhydrous lower alcohol, preferably a lower alcohol such as methanol or ethanol, to form the corresponding diester-diacid, which is then hydrogenated at about 20°-30° C. and 50-600 psi until the rate of hydrogen uptake decreases sharply. Higher temperatures and pressure may lead to hydrogenolysis of the hydroxyl group. After removal of the catalyst, the polyamine, terminating primary amine, and solvent (e.g., 1-methyl-2-pyrrolidione) are then added and the excess alcohol distilled off, preferably under moderate vacuum. The polymerization begins at about 100° C. The products (i.e., alcohol and water) are distilled off, either by using a moderate vacuum and a temperature below the boiling point of the solvent or by adding a water-insoluble solvent, such as toluene, and collecting the water-alcohol mixture in a Dean-Stark water trap. For the latter technique to work well a water-soluble, lower alcohol, preferably methanol, should be formed as the by-product.

The polyepoxides useful herein may be substituted or unsubstituted aliphatic, cycloaliphatic, aromatic and/or heterocyclic polyepoxides, such as glycidyl esters, glycidyl ethers, glycidyl amines, or epoxidized olefins. They may be substituted with non-interfering substituents such as halogen, hydroxyl, and other groups.

U.S. Pat. Nos. 2,633,458 (issued Mar. 31, 1953 to E. C. Shokal); 3,547,885 (issued Dec. 15, 1970 to M. F. Dante et al.); 3,562,213 (issued Feb. 9, 1971 to M. J. Collins); 3,746,686 (issued July 17, 1973 to C. D. Marshall et al.); and 4,066,625 (issued Jan. 3, 1978 to J. C. Bolger) describe suitable polyepoxides. Especially useful are liquid and solid aromatic diepoxides, such as glycidyl polyethers having epoxide equivalent weights of 175-4000, preferably 175-1200. The preferred polyepoxides are the aromatic glycidyl polyethers formed by reacting an epihalohydrin with dihydric phenols such as 4,4'-isopropylidenebis(2,6-dibromophenol), 1,1-bis(4-hydroxyphenyl)ethane, bis(4-hydroxyphenyl)methane, 4,4'-dihydroxydiphenyl sulphone, hydroquinone, resorcinol, dihydroxydiphenyl, and dihydroxynaphthalene.

Especially useful are the glycidyl polyethers prepared from epichlorohydrin and 4,4'-isopropylidenediphenol (bisphenol A). The molecular weight, softening point, and viscosity generally depend on the ratio of epichlorohydrin to 4,4'-isopropylidenediphenol used in the preparation of the glycidyl polyether. The polyethers may be liquids (viscosity dependent on n) having epoxide equivalent weights from 175 to 280 or solids having softening points between 50° and 170° C. and epoxide equivalent weights from 385 to above 4,000. Preferred glycidyl polyethers are those having epoxide equivalent weights of 175–600.

When the epoxide-reactive group on the polyimide is a phenol, it will react with the epoxide to form a hydroxy ether. When it is a carboxylic acid group, it will react to form a hydroxy ester. When it is an amine group, it will react to form a hydroxy substituted amine. When it is a thiol group, it will react to form a hydroxy thioether. The epoxide reactions with phenol- and carboxylic acid-terminated groups generally require a catalyst. The preferred catalysts are those which have little tendency to cause side reactions. Typical side reactions are a ring opening polymerization of the epoxy groups and reaction of the epoxy groups with non-aromatic hydroxyl groups. Preferred catalysts are hindered tertiary amines, e.g., tributylamine. Especially preferred are phosphine derivatives, e.g., triphenylphosphine. The adducts are prepared by heating solutions of the polyimide, polyepoxide, and catalyst at temperatures of 120°–200° C., preferably 140°–170° C. A particularly desirable solvent is tetrahydrofuran since it is low boiling and easy to remove from the adduct. With this solvent the reaction must be run in a pressure vessel. The extent of reaction may be followed by measuring the inherent viscosity. The value first increases and usually levels off as the reaction proceeds.

The adducts may be cured by heating, preferably in the presence of epoxy curing catalysts such as N,N-dimethylbenzylamine. Heat curing may be carried out at about 150° C. for about 1 hour, preferably at about 120° C. for about 0.75 hour, to remove the solvent, followed by a further cure for about 2 hours at about 175° C. Longer curing times at lower temperatures and shorter curing times at higher temperatures may be used, and it is within the skill of one in the art to determine appropriate curing times and temperatures.

It can be appreciated that a large number of variations may be effected in preparation of the polyimide, such as the selection of starting materials and molar ratios, and in the selection of the polyepoxide, as well as in the preparation and use procedures herein, without materially departing from the scope and spirit of the invention. Such variations will be apparent to those skilled in the art and are to be included within the scope of this invention.

In the examples which follow, all parts and percentages are given by weight and all temperatures are in degrees Celsius unless otherwise noted. Inherent viscosities are determined on 1 g./dl. solutions of polymer in 1-methyl-2-pyrrolidinone (also referred to as N-methyl pyrrolidinone) at 25° C. The softening point is measured in a Fischer-Johns melting point apparatus.

EXAMPLE I

This example describes the preparation of a phenol-, carboxyl-, and amine-terminated polyimide oligomer.

PART A

Preparation of the Carbinol-Containing Tetracarboxylic Acid Compound

A total of 483.4 g. (1.5 moles) of 3,3',4,4'-benzophenonetetra-carboxylic dianhydride (also referred to as 4,4'-carbonyl diphthalic anhydride) was refluxed with stirring for 2 hours with 800 ml. of methanol. The solution was cooled and charged to a 2 l. autoclave along with 200 ml. of additional methanol and 12 g. of 5% palladium on activated carbon. Hydrogenation of the resulting bis(methyl half-ester) of 3,3',4,4'-benzhydrophenone tetracarboxylic acid was carried out at about 25° C. and 400 psi until the rate of hydrogen uptake virtually ceased. The mixture was gravity filtered to remove the hydrogenation catalyst; the filter paper and its contents were washed with fresh methanol and all washings were combined. The active concentration was determined by titration with 0.1N sodium hydroxide to a phenolphthalein end point.

PART B

Preparation of A Phenol-Terminated Polyimide Oligomer (n=1, m=0)

A 500 ml. round bottom 4-neck flask was charged with 0.2 mole (0.4 acid equivalents) of the above solution containing the half-ester, 0.1 mole of 2,4-toluenediamine, 0.2 mole of m-aminophenol, and 160 ml. of 2-methoxyethyl ether. The excess methanol was removed by vacuum distillation up to a pot temperature of 80° C. and a vacuum of 40 mm. Hg. A total of 60 ml. of heptane was added, and the flask was fitted with a 25 ml. Dean Stark receiver. The solution was heated to reflux until the water/methanol by-product of the reaction ceased to evolve (about 5.5 hours). The solution was cooled and the polymer was precipitated in water. It was filtered, washed with water, and vacuum dried at 110° C. The resulting oligomer had an inherent viscosity of 0.076 and a softening point of 178°–182° C.

PART C

Preparation of A Carboxyl-Terminated Polyimide Oligomer (n=1, m=1)

The reaction was carried out as in Part B but using 0.2 mole of the half-ester and 0.3 mole of 2,4-toluenediamine. After the water evolution was complete, 0.2 mole of the trimellitic anhydride was added and the reaction completed to form a carboxyl-terminated polyimide. The product was precipitated in water. It had a softening point of 260°–270° C.

PART D

Preparation of An Amine-Terminated Polyimide Oligomer (n=2, m=0)

The reaction was carried out as in Part B but using 0.18 mole of the half-ester and 0.24 mole of 1,3-bis(3-aminophenoxybenzene).

EXAMPLE II

This example describes the preparation of polyimide-polyepoxide adducts using the above terminated polyimide oligomers and a solid epoxy resin.

A total of 27.5 g. (0.03 mole) of the polyimide of Part B of Example I (having a softening point of 178°–82° C.), 57.4 g. (0.066 mole) of the diglycidyl ether of tetrabromobisphenol A (a solid epoxy resin sold by Dow Chemical Co. under the trademark DER 542 which had an epoxide equivalent weight of 435 and reported softening point of about 50°–62° C.), and 1.1 ml. of tributylamine was dissolved in 85 ml. tetrahydrofuran (THF). The solution was sealed in a 250 ml. autoclave and heated for 5 hours at about 150°–160° C. The inherent viscosity was 0.13. A portion of the adduct was recovered by evaporating the solution to dryness (1 hour at 150° C.). The dry adduct had an inherent viscosity of 0.13 and a softening point of 156°–160° C.

The polyimide of Part C of Example I (having a softening point of 260°-70° C.) was reacted in the same way except that 32.3 g. (0.025 mole) of the polyimide, 47.9 g. (0.055 mole) of the diglycidyl ether of tetrabromobisphenol, 0.8 g. tributylamine, and 80 g. tetrahydrofuran were used. The inherent viscosity was 0.09. The adduct, after drying for 1 hour at 150° C., had an inherent viscosity of 0.10 and a softening point of 220°-230° C.

The polyimide of Part D of Example I was reacted in the same way except that the reaction was carried out for 2.5 hours at 140° C. without catalyst. The adduct had a inherent viscosity of 0.14. The adduct, after drying for 1 hour at 150° C., was crosslinked. It was observed to soften at 130°-135° C.

EXAMPLE III

Additional polyimide oligomers (n=1-2, m=0) terminated with m-aminophenol were prepared and reacted with the solid epoxide resin of Example II. The polyimides were prepared using the procedure of Example I except that the indicated diamine was used in the preparation. The n value and softening point of the polyimides are given in Table I together with data on the properties of the polyimide-polyepoxide adduct.

TABLE I

| | Carbinol-Containing Polyimide Terminated with m-Aminophenol | | | Polyimide (PI)/ Polyepoxide (PE) Adduct | | |
|---|---|---|---|---|---|---|
| Designation | Diamine | n | Softening Point (°C.) | Inherent Viscosity* | Softening Point (°C.) | Solubility in |
| A | none | 0 | 182-185 | 0.075 | 112-115 | THF |
| B | 4,4'-oxydianiline | 1 | 198-205 | 0.068 | 125-135 | NMP |
| C | 3,3'-sulfonyldianiline | 1 | 200-203 | 0.059 | 135-138 | THF |
| D | 1,6-hexanediamine | 1 | 145-150 | 0.099 | 125-128 | THF |
| E | 1,6-hexanediamine | 2 | 154-157 | 0.130 | 128-131 | THF |
| F | 2,4-toluenediamine | 2 | 224-227 | 0.130 | 175-179 | THF |
| G | diethyltoluenediamine | 1 | 175-180 | 0.091 | 155-158 | THF |
| H | diethyltoluenediamine | 2 | 200-204 | 0.130 | 160-164 | THF |

THF is tetrahydrofuran.
*Measured before drying
Diethyltoluenediamine is a mixture of two isomers - (available from Ethyl Corp.)

The results show that the polimides can be reacted with the epoxide to yield adducts which are typically still soluble in the organic solvent. They further show the adducts have significantly higher softening points than the polyepoxide but lower than the polyimide oligomer. The adducts have softening points ranging from 112°-170° C., whereas the polyepoxides have softening points of 50°-62° C. and the polyimides have softening points of 145°-227° C.

EXAMPLE IV

This example shows the preparation of polyimide oligomers (n=1-4, m=0) terminated with other phenol-containing amines as well as a carboxyl-containing amine and the preparation of the polyepoxide adducts thereof. It also shows the use of other polyepoxides and differing polyimide to polyepoxide ratios. The results are shown in Table II. The inherent viscosities of the adducts were measured before drying.

TABLE II

| | Terminated Carbinol-Containing Polymide[a] | | | |
|---|---|---|---|---|
| Designation | Diamine | Terminating Amine | n | Softening Point (°C.) |
| I | 2,4-toluenediamine | p-aminophenol | 1 | 173-178 |
| J | 2,4-toluenediamine | m-aminophenol | 1 | 168-172 |
| K | 2,4-toluenediamine | m-aminophenol | 2 | 215-218 |
| L | 2,4-toluenediamine | m-aminophenol | 3 | 196-198 |
| M | 2,4-toluenediamine | m-aminophenol | 4 | 220 |
| N | 2,4-toluenediamine | m-aminophenol | 2 | 224-227 |
| O | 2,4-toluenediamine | m-aminobenzoic acid | 1 | 207-208 |

| Polyimide/ Polyepoxide[b] | PI/PE Adduct | | |
|---|---|---|---|
| | PI/PE Ratio | Softening Point (°C.) | Inherent Viscosity |
| I/DER 542 | 1/2.2 | 146-150 | 0.10 |
| J/EPON 828 | 1/2.2 | c. | 0.17 |
| K/DER 542 | 2/3 | 185-188 | 0.07 |
| L/DER 542 | 1/2.2 | 183-185 | 0.10 |
| M/DER 542 | 1/2.2 | 195-198 | 0.13 |
| N/EPON 828 | 1/2.2 | 140-143 | 0.10 |
| O/DER 542 | 1/2.2 | 160-165 | 0.11 |

[a].All of the terminated polyimide/polyepoxide adducts except the one designated N were prepared using tributylamine as the catalyst. N was prepared usuing triphenylphosphine as the catalyst.
[b].DER 542 is described in Example II; Epon 828 is a liquid bisphenol A type polyepoxide marketed by Shell Chemical Co.
[c].Reaction temperature was reduced from 150-160° C. to 135° C. to give a controllable reaction. The adduct crosslinked on drying. It was observed to soften at 130-134° C.

EXAMPLE V

This example demonstrates that the adducts cure to an insoluble crosslinked product.

The adducts designated F and N (see Table I and II) at 62% and 56% solids in THF were diluted with an equal weight of THF and then treated with 3% 1,2-dimethylimidazole (based on polyimide-polyepoxide). A portion of each solution was dried overnight at room temperature and then heated for 1 hour at 175° C. The products were insoluble in THF indicating they had crosslinked.

EXAMPLE VI (COMPARATIVE)

A polyimide (n=1, m=0) containing no carbinol groups was prepared using 3,3',4,4'-benzophenone tetracarboxylic dianhydride, 1,6-hexanediamine, and m-aminophenol. The polyimide (softening point 166°-170° C) was insoluble in THF. The polyimide was reacted with an excess of the polyepoxide DER 542 dissolved in THF. The adduct was likewise insoluble.

EXAMPLE VII (COMPARATIVE)

A polyimide (n=1) containing carbinol groups but end-capped with an amine that contained no epoxide-reactive functional group was prepared using the bis(methyl half-ester) of 3,3',4,4'-benzhydrol tetracarboxylic acid, 2,4-toluenediamine, and aniline. The resulting polyimide (softening point 180°-183° C.) was soluble in THF. An attempt was made to react the polyimide with the polyepoxide DER 542. After 5 hours at 160° C. only a mixture of a liquid and insoluble solid resulted. The inherent viscosity of the soluble portion was only 0.028.

EXAMPLE VIII

The compositions of Example V are used to glue steel pieces by coating the surfaces to be glued with the solutions containing the adducts and 1,2-dimethylimidazole curing agent. The solvent is evaporated off in a forced-ventilation oven for 15 minutes at 50° C. The coated surfaces are combined and the assemblies are cured at a temperature above the softening point of the adducts (i.e., above 175°–79° for F and above 140°–43° for N).

Now that the preferred embodiments of the invention have been described in detail, various modifications and improvements thereon will become readily apparent to those skilled in the art. Accordingly, the spirit and scope of the present invention are to be limited only by the appended claims, and not by the foregoing specification.

What is claimed is:

1. A carbinol-containing polyimide oligomer terminated with epoxide-reactive end groups, which has the structure

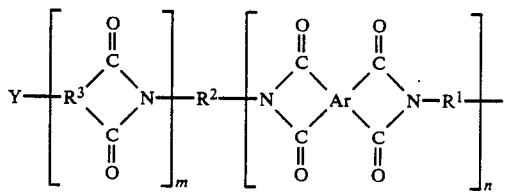

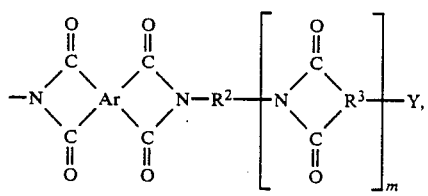

wherein Ar is

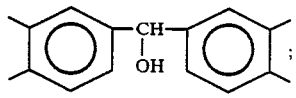

$R^1$ and $R^2$ are independently divalent organic radicals; $R^3$ is a trivalent organic radical; Y is an epoxide-reactive group selected from the group consisting of a phenol or thiol m is 0 and 1 and n is 0–10.

2. The polyimide oligomer of claim 1, wherein m is 0, n is 1–10, and Y is the phenol group.

3. The polyimide oligomer of claim 2, wherein $R^1$ is the residue of a diamine selected from the group consisting of 4,4'-oxydianiline, 3,3'-sulfonyldianiline, 1,6-hexanediamine, 2,4-toluenediamine, and diethyltoluenediamine.

4. The polyimide oligomer of claim 3, wherein n is 1–5 and the phenol-containing group Y—$R^2$— is the residue of m-aminophenol or p-aminophenol.

5. The polyimide oligomer of claim 3, wherein the diamine is 2,4-toluenediamine or diethyltoluenediamine.

6. The polymide oligomer of claim 5, wherein the diamine is 2,4-toluenediamine.

7. The polymide oligomer of claim 5, wherein the diamine is diethyltoluenediamine.

* * * * *